United States Patent
Sugiura (10) Patent No.: US 11,267,486 B2
(45) Date of Patent: Mar. 8, 2022

(54) VEHICLE DRIVING CONTROL SYSTEM AND VEHICLE DRIVING CONTROL METHOD

(71) Applicant: ISUZU MOTORS LIMITED, Tokyo (JP)

(72) Inventor: Koji Sugiura, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 220 days.

(21) Appl. No.: 16/612,539

(22) PCT Filed: May 11, 2018

(86) PCT No.: PCT/JP2018/018271
§ 371 (c)(1),
(2) Date: Nov. 11, 2019

(87) PCT Pub. No.: WO2018/207905
PCT Pub. Date: Nov. 15, 2018

(65) Prior Publication Data
US 2020/0122746 A1 Apr. 23, 2020

(30) Foreign Application Priority Data
May 11, 2017 (JP) .............................. JP2017-094575

(51) Int. Cl.
*B60W 60/00* (2020.01)
*B60W 40/08* (2012.01)
(Continued)

(52) U.S. Cl.
CPC ........... *B60W 60/0018* (2020.02); *A61B 5/18* (2013.01); *A61B 5/318* (2021.01); *A61B 5/369* (2021.01);
(Continued)

(58) Field of Classification Search
CPC ............ B60W 60/0018; B60W 40/08; B60W 2540/229; B60W 2540/221;
(Continued)

(56) References Cited

U.S. PATENT DOCUMENTS 6,575,902 B1* 6/2003 Burton ...................... B60T 7/12
600/300
2004/0046666 A1* 3/2004 Yasuchi ............... A61B 5/0245
340/573.1
(Continued)

FOREIGN PATENT DOCUMENTS

CN 1572575 A 2/2005
CN 105072986 A 11/2015
(Continued)

OTHER PUBLICATIONS

Picot et al., On-Line Detection of Drowsiness Using Brain and Visual Information, May 2012, IEEE, IEEE Transactions on Systems, Man, and Cybernetics—Part A: Systems and Humans, vol. 42, No. 3 (Year: 2012).*

(Continued)

*Primary Examiner* — Nadeem Odeh
(74) *Attorney, Agent, or Firm* — Procopio, Cory, Hargreaves & Savitch LLP (57) ABSTRACT

Control is performed so as to detect a brain wave or a heartbeat of a driver of a vehicle during automatic driving of the vehicle, and use a plurality of indexes further correlated with sleepiness of the driver among indexes related to the brain wave or the heartbeat of the driver to calculate a concentration index CI, which is an index indicating driving concentration of the driver, at each preset control interval.

9 Claims, 8 Drawing Sheets

(51) Int. Cl.
*A61B 5/18* (2006.01)
*A61B 5/00* (2006.01)
*A61B 5/318* (2021.01)
*A61B 5/369* (2021.01)
*B60Q 1/46* (2006.01)

(52) U.S. Cl.
CPC ............ *A61B 5/6893* (2013.01); *B60W 40/08* (2013.01); *B60Q 1/46* (2013.01); *B60W 2040/0827* (2013.01); *B60W 2540/221* (2020.02); *B60W 2540/229* (2020.02)

(58) Field of Classification Search
CPC ...... B60W 2040/0827; B60W 60/0053; A61B 5/318; A61B 5/369; A61B 5/18; A61B 5/6893; A61B 5/7246; A61B 5/4809; A61B 5/7264; B60Q 1/46; G08B 21/06; G08G 1/16
See application file for complete search history.

(56) References Cited

U.S. PATENT DOCUMENTS

| | | | |
|---|---|---|---|
| 2004/0243013 | A1 | 12/2004 | Kawachi et al. |
| 2014/0167968 | A1 | 6/2014 | Tuzsuzov |
| 2016/0029940 | A1 | 2/2016 | Iizuka et al. |
| 2016/0362113 | A1* | 12/2016 | Takaso ................. G05D 1/0255 |
| 2017/0313319 | A1* | 11/2017 | Kishi ................... G05D 1/0248 |
| 2017/0364070 | A1 | 12/2017 | Oba |
| 2019/0004513 | A1 | 1/2019 | Chiba et al. |
| 2019/0271981 | A1 | 9/2019 | Oba |

FOREIGN PATENT DOCUMENTS

| | | |
|---|---|---|
| CN | 105243789 A | 1/2016 |
| FR | 1559384 A | 3/1969 |
| JP | H04-250171 A | 9/1992 |
| JP | 2009-232990 A | 10/2009 |
| JP | 2014-515129 A | 6/2014 |
| JP | 2016-088497 A | 5/2016 |
| JP | 2016-115356 A | 6/2016 |
| JP | 2016-215658 A | 12/2016 |
| JP | 2017-004210 A | 1/2017 |
| JP | 2017-019424 A | 1/2017 |
| WO | 2017-022417 A1 | 2/2017 |

OTHER PUBLICATIONS

First Office Action for related CN App No. 201880030765.6 dated Nov. 4, 2020, 43 pgs.

International Search Report and Written Opinion for related International Application No. PCT/JP2018/018271, dated Jun. 12, 2018; English translation of ISR provided (9 pages).

"Get Close to Rail Driver: Stepping on Pedal Every 30 Seconds and Dancing With Signals", Wenzhou City Newspaper, https://zj.zjol.com.cn/news/251272.html?/ismobilephone=1&t=1557648324044, Retrieved Sep. 1, 2021, pp. 1-4. (e.g., see p. 9, lines 7-14 of CN OA).

Second Office Action for related CN App No. 201880030765.6 dated Jul. 6, 2021; English translation of CN OA provided, 35 pages.

* cited by examiner

VEHICLE DRIVING CONTROL SYSTEM AND VEHICLE DRIVING CONTROL METHOD

CROSS-REFERENCE TO RELATED APPLICATIONS

This application is a U.S. National Stage entry of PCT Application No: PCT/JP2018/018271 filed on May 11, 2018, which claims priority to Japanese Patent Application No. 2017-094575, filed May 11, 2017, the contents of which are incorporated herein by reference.

TECHNICAL FIELD

The present disclosure relates to a vehicle driving control system and a vehicle driving control method.

BACKGROUND ART

In recent years, research and development of techniques for automatically driving a vehicle by a driving control system placed on an automobile, regardless of an operation of a driver, has been carried out (see, for example, PTL 1). Meanwhile, there is a technique of using a pupil width or heartbeat of a driver to monitor an awakening degree of the driver, and transmitting a periodic audio signal to the driver when the awakening degree is low (see, for example, PTL 2).

CITATION LIST

Patent Literature

PTL 1: JP-A-2016-215658
PTL 2: JP-A-2014-515129

SUMMARY OF INVENTION

Technical Problem

When the vehicle is automatically driven (automatic driving) by the system, since the driver is released from driving operations, the driver may become sleepy and concentration with respect to driving (driving concentration) tends to decrease. When a sudden situation occurs, for example, when a vehicle driven ahead suddenly decelerates and an inter-vehicle distance between the vehicle ahead and the given vehicle suddenly decreases, it is necessary to forcibly transfer driving authority of the vehicle from the system to the driver, if the driving concentration of the driver is low, the driver may delay an driving operation necessary for the transfer (driving switching), which may make it difficult to safely and quickly transfer the driving authority of the vehicle from the system to the driver. Therefore, even when the vehicle is driven automatically, it is important that the driving concentration of the driver is maintained to some extent.

Meanwhile, in order to maintain the driving concentration of the driver to some extent, it is necessary to accurately grasp the driving concentration. In particular, when the vehicle is driven automatically, since a main factor causing the decrease in the driving concentration is sleepiness, it is necessary to grasp that the driving concentration is closely related to the sleepiness of the driver.

However, a method of calculating the driving concentration of the driver while closely reflecting the sleepiness of the driver has not been established.

An object of the present disclosure is to provide a vehicle driving control system and a vehicle driving control method, which can calculate driving concentration of a driver of a vehicle with high accuracy and can maintain the driving concentration of the driver to some extent even when the vehicle is driven automatically.

Solution to Problem

A vehicle driving control system according to the present disclosure for achieving the above object is a vehicle driving control system which has a function of automatically driving a vehicle. A control device which controls the driving control system performs control so as to detect a brain wave or a heartbeat of a driver of the vehicle during automatic driving of the vehicle, and use a plurality of indexes further correlated with sleepiness of the driver among indexes related to the brain wave or the heartbeat of the driver to calculate a concentration index, which is an index indicating driving concentration of the driver, at each preset control interval.

A vehicle driving control method according to the present disclosure for achieving the above object is a vehicle driving control method which has a function of automatically driving a vehicle, in which control is performed so as to detect a brain wave or a heartbeat of a driver of the vehicle during automatic driving of the vehicle, and use a plurality of indexes further correlated with sleepiness of the driver among indexes related to the brain wave or the heartbeat of the driver to calculate a concentration index, which is an index indicating driving concentration of the driver, at each preset control interval.

Advantageous Effects of Invention

According to the present disclosure, since the brain wave or the heartbeat of the driver of the vehicle is detected during the automatic driving of the vehicle when the driver tends to feel sleepy (tends to drive inattentively), and the concentration index which is the index indicating the driving concentration of the driver is calculated using the plurality of indexes closely correlated with the sleepiness of the driver, appropriate measures can be performed to maintain the driving concentration of the driver to some extent based on the calculated concentration index, and the driving concentration of the driver can be maintained to some extent even during automatic driving of the vehicle.

As a result, the driving concentration of the driver is maintained to some extent, so that the driver can perform appropriate driving operations, and the vehicle driving authority can be safely and quickly transferred when it is necessary to forcibly transfer the vehicle driving authority from the system to the driver.

DESCRIPTION OF EMBODIMENTS

Figure 8:
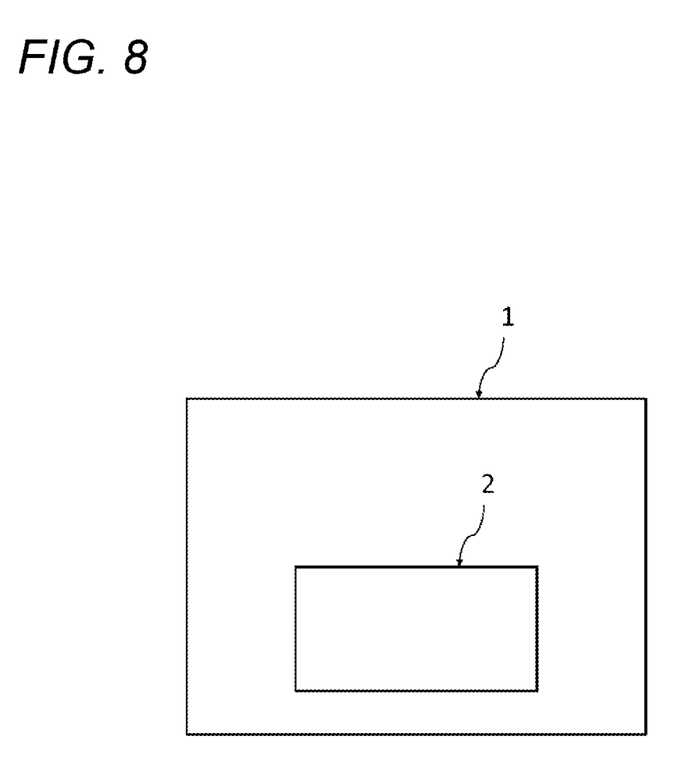
FIG. 8 schematically shows an outline of a driving control system 1 according to the present disclosure.

Hereinafter, a vehicle driving control system and a vehicle driving control method according to the present disclosure will be described based on an embodiment shown in the drawings. A vehicle including a vehicle driving control system 1 according to the present disclosure has an automatic driving function that allows the vehicle 3 to be driven automatically based on the driving control system 1 without following a driving operation of a driver. That is, either the driver or the driving control system 1 has driving authority for the vehicle. As shown in FIG. 8, the vehicle is provided with a control device 2 that controls the driving control system 1.

Figure 1:
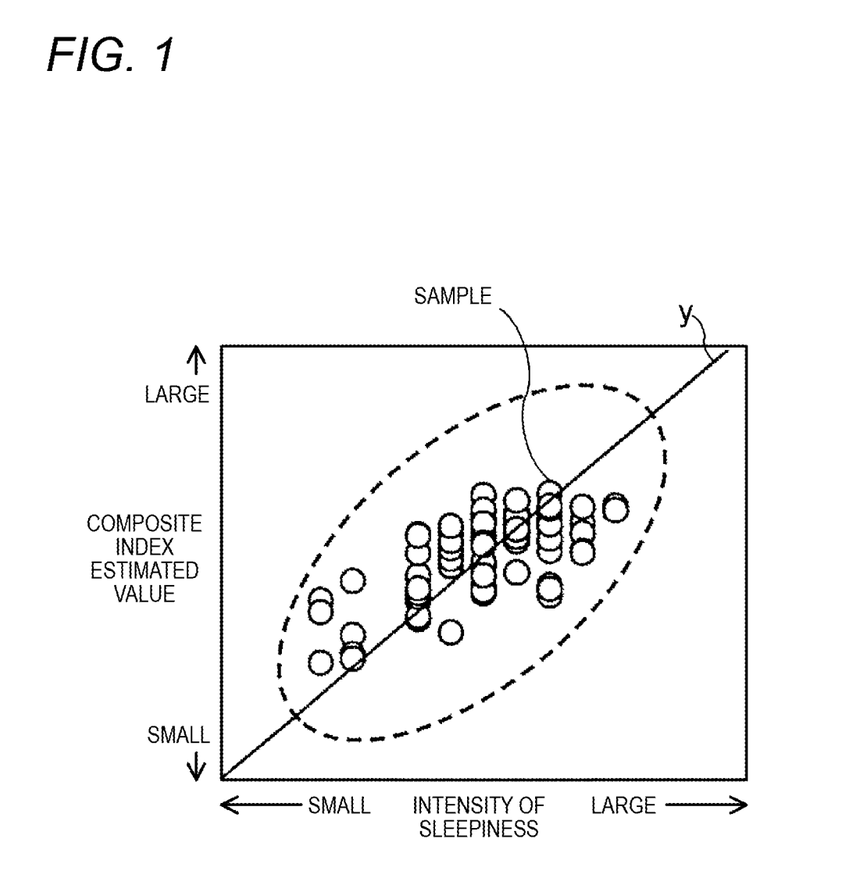
FIG. 1 shows a correlation between an estimated value of a concentration index and an intensity of sleepiness.

In the present disclosure, the control device 2 performs control so as to detect a brain wave or a heartbeat of the driver of the vehicle during automatic driving of the vehicle, and uses a plurality of (two or more) indexes further correlated with sleepiness of the driver among indexes related to the brain wave or the heartbeat of the driver to calculate a concentration index (composite index) CI, which is an index indicating driving concentration of the driver, at each preset control interval (such as time interval or driving distance interval). As shown in FIG. 1, the concentration index CI has a positive correlation with intensity of sleepiness of the driver, and the concentration index CI increases as the intensity of sleepiness of the driver increases.

A standard deviation of brain wave α waves, an average of brain wave β waves, an average of heartbeat peak value intervals and a standard deviation of heartbeat peak value intervals are used as the indexes correlated with the sleepiness of the driver.

Figure 2:
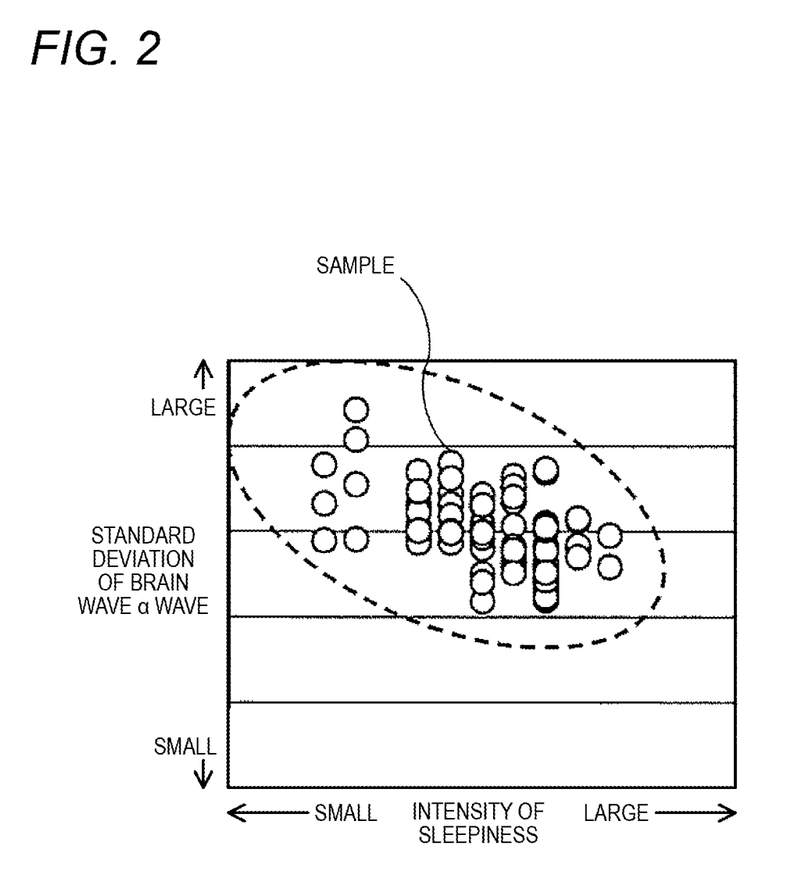
FIG. 2 shows a correlation between a standard deviation of brain wave $\alpha$ waves of a driver and the intensity of sleepiness.

The brain wave α wave is a brain wave of 8 to 13 Hz, which is likely to occur when the driver is in a relaxed state. When consciousness of the driver is clear, a deviation of the brain wave α waves (standard deviation of the brain wave α waves) within a certain time (time set in advance according to experiments) is large. Meanwhile, when the consciousness of the driver is uncertain and the driver feels sleepy, the standard deviation of the brain wave α waves is small That is, as shown in FIG. 2, the standard deviation of the brain wave α waves has a negative correlation with the sleepiness of the driver, and the standard deviation of the brain wave α waves decreases as the intensity of sleepiness of the driver increases.

Figure 3:
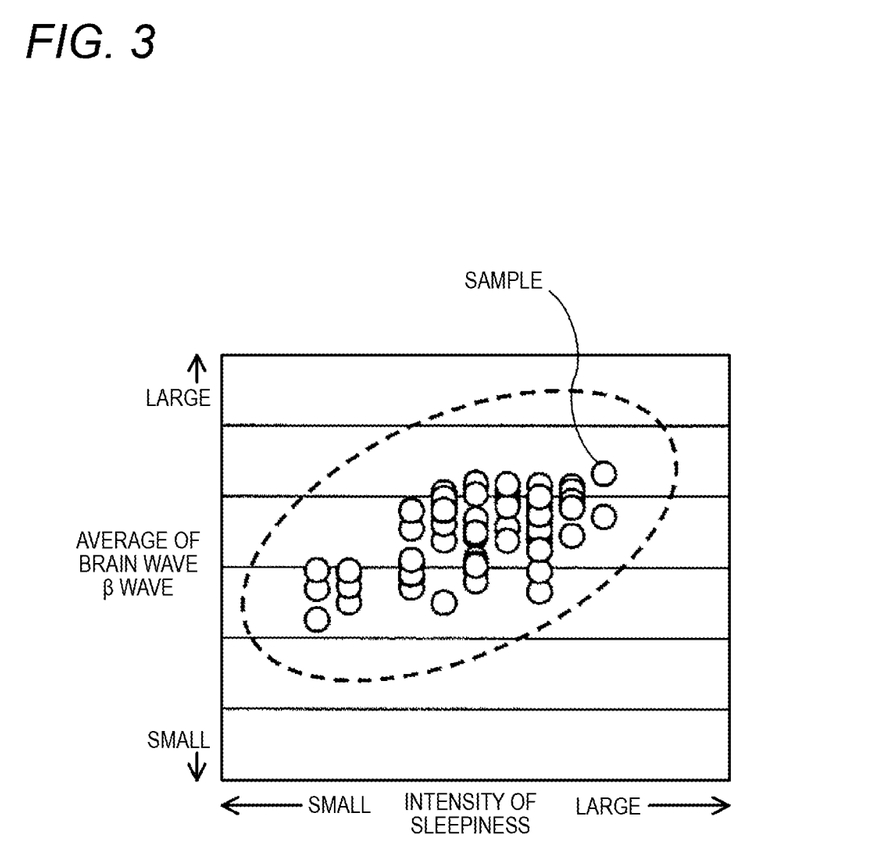
FIG. 3 shows a correlation between an average of brain wave $\beta$ waves of the driver and the intensity of sleepiness.

The brain wave β wave is a brain wave of 13 to 25 Hz, which is likely to occur when the driver is in an active state (tension state). As the sleepiness of the driver increases, the driver begins an awakening effort to get rid of the sleepiness. As the sleepiness increases, the awakening effort increases, and the tension state of the driver increases. In such a state, the average of the brain wave β waves within a certain time (average of the brain wave β waves) increases. That is, as shown in FIG. 3, the average of the brain wave β waves has a positive correlation with the sleepiness of the driver.

The brain wave α wave and β wave are time-series data of a target frequency obtained by passing brain waves derived from a central part (Cz part) of a brain of the driver using an international 10-20 method through a band pass filter, and are calculated as activity of the target frequency. The international 10-20 method refers to a method in which measurement electrodes are disposed at equal intervals on an entire scalp of a human (driver) while reference electrodes are disposed on earlobes to measure a potential difference between the measurement electrodes and the reference electrodes.

Figure 4:
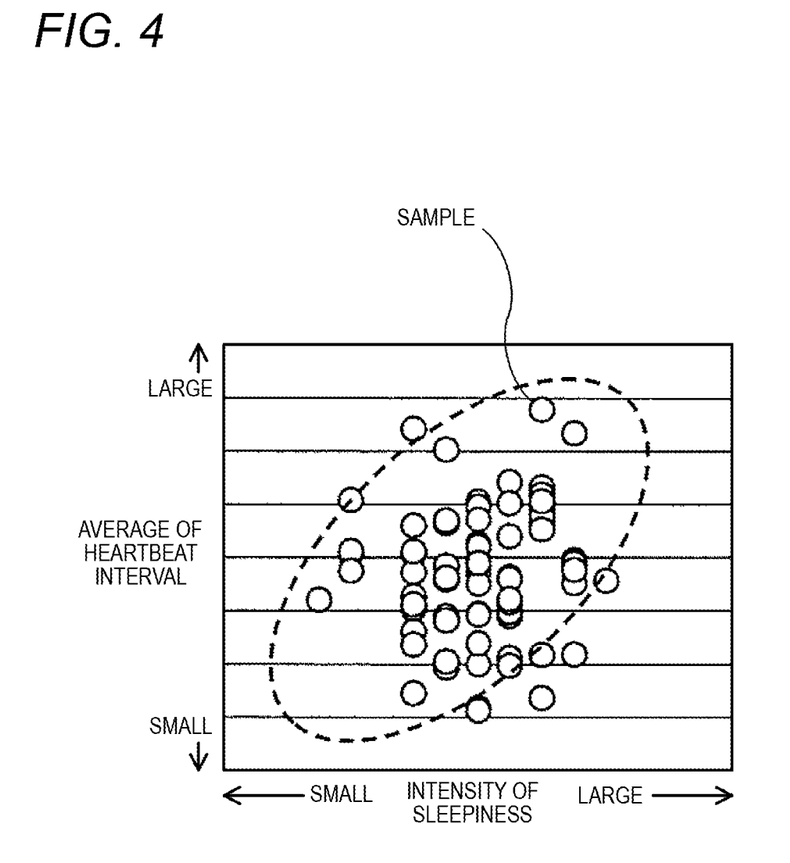
FIG. 4 shows a correlation between an average of heartbeat peak value intervals of the driver and the intensity of sleepiness.

The heartbeat peak value interval refers to an interval between peaks of adjacent waves of heartbeat in an electrocardiogram. As the driver feels sleepy, the heartbeat is relatively low, and the heartbeat peak value interval increases. That is, as shown in FIG. 4, the heartbeat peak value interval has a positive correlation with the sleepiness of the driver.

Figure 5:
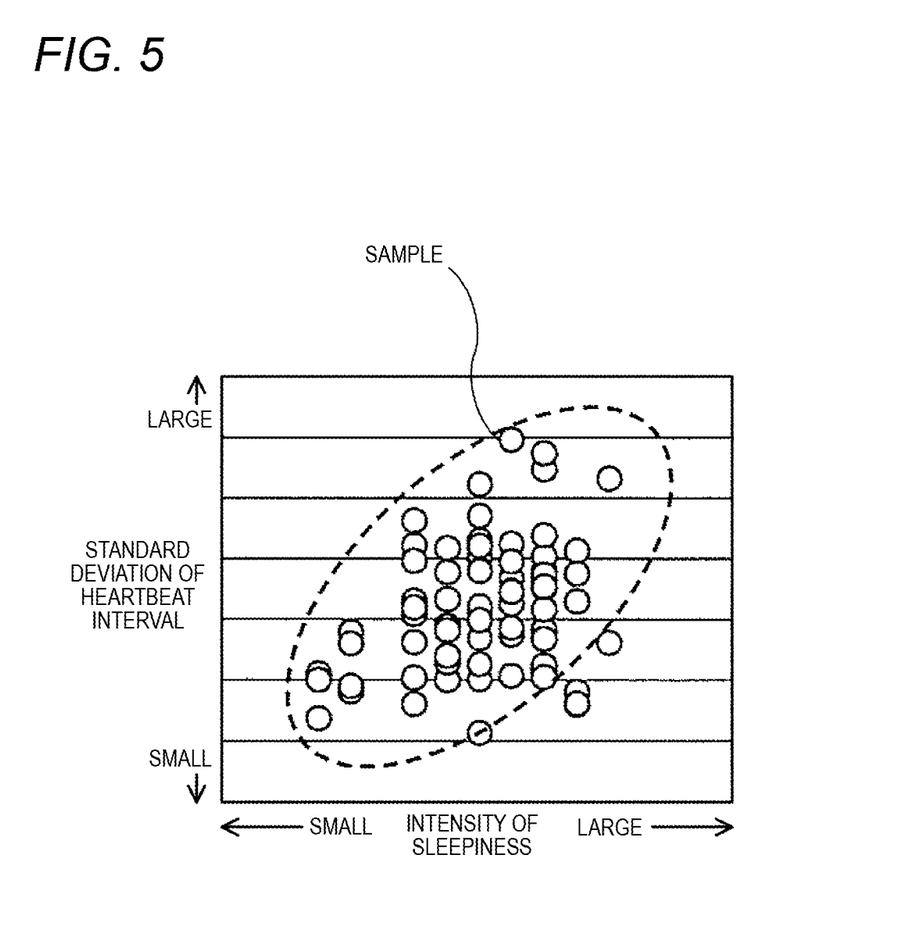
FIG. 5 shows a correlation between a standard deviation of the heartbeat peak value intervals of the driver and the intensity of sleepiness.

The standard deviation of the heartbeat peak value intervals is a variation of the heartbeat peak value intervals within a certain time. The heartbeat peak value intervals become larger as the driver feels sleepy, fluctuation of the heartbeat peak value intervals becomes larger, and the standard deviation becomes larger. That is, as shown in FIG. 5, the standard deviation of the heartbeat peak value interval has a positive correlation with the sleepiness of the driver.

By using the above four indexes, that is, the standard deviation of the brain wave α waves of the driver, the average of the brain wave β waves, the average of the heartbeat peak value intervals and the standard deviation of the heartbeat peak value intervals, as the indexes correlated with the sleepiness of the driver, the concentration index CI calculated as the composite index can be used as an index reflecting the sleepiness of the driver.

A method of calculating the concentration index CI will be described. When the concentration index CI is calculated using the four indexes (the standard deviation of the brain wave α waves of the driver, the average of the brain wave β waves, the average of the heartbeat peak value intervals and the standard deviation of the heartbeat peak value intervals), an estimated value y of the concentration index CI is calculated using, for example, the following linear expression. This linear expression can be expressed in a form of "$y = a + \alpha_1 \times x_1 + \alpha_2 \times x_2 + \alpha_3 \times x_3 + \alpha_4 \times x_4$", in which a refers to an intercept value, $x_1$ refers to the standard deviation of the brain wave α waves, $x_2$ refers to the average value of the brain wave β waves, $x_3$ refers to the average value of the heartbeat peak value intervals, $x_4$ refers to the standard deviation of the heartbeat peak value intervals and $\alpha_1$, $\alpha_2$, $\alpha_3$ and $\alpha_4$ refer to coefficients. Since a, $\alpha_1$, $\alpha_2$, $\alpha_3$, and $\alpha_4$ are fixed values set in advance according to experiments or the like, the estimated value y of the concentration index CI is calculated by substituting measured values $x_1$, $x_2$, $x_3$, and $x_4$ into this linear expression. The coefficient $\alpha_1$ is a negative value.

Figure 6:
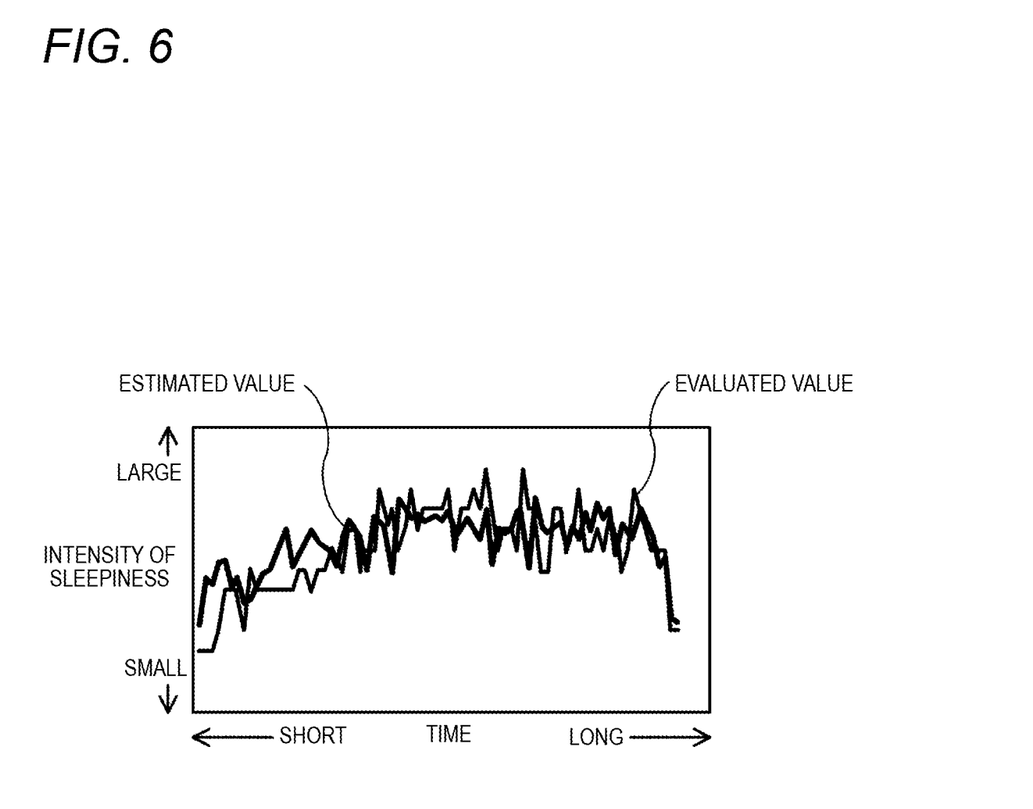
FIG. 6 shows a correlation between the estimated value and an evaluation value of the concentration index.

As shown in FIG. 6, an estimated value y1 of the calculated concentration index CI and an evaluation value which is an estimated value of the intensity of sleepiness of the driver estimated based on a facial expression of the driver are transition lines which are approximate. A correlation coefficient between the two estimated values may be approximately 0.7, and there is a strong positive correlation therebetween.

As described above, in the present disclosure, since the concentration index CI which is the index indicating the driving concentration of the driver is calculated using the plurality of indexes closely correlated with the sleepiness of the driver during the automatic driving of the vehicle when the driver tends to feel sleepy (tends to drive inattentively), appropriate measures can be performed to maintain the driving concentration of the driver to some extent based on the calculated concentration index CI.

The concentration index CI may be calculated using, in addition to the above four indexes, a biological index of a different driver and an image analysis information of the driver. In this case, the estimated value y of the concentration index CI is calculated using a linear expression of "$y = a + \alpha1 \times x1 + \alpha2 \times x2 + \alpha3 \times x3 + \alpha4 \times x4 + \alpha5 \times x5 + \alpha6 \times x6$", in which x5 refers to the biological index of the driver, x6 refers to the image analysis information of the driver, and $\alpha5$, $\alpha6$ refers to coefficients.

The biological index can be, for example, a change in a seat pressure of the driver. When a change in a body pressure distribution is obtained by a pressure sensor embedded in a seat surface of the driver, it is considered that the driver is sleepy and is in a state where physical activity is low, that is, the change in the pressure is low. At this time, as the driver feels sleepy, an amount of change in the pressure decreases, and there is a negative correlation with the sleepiness of the driver.

The image analysis info nation of the driver is information obtained by image analysis of a face photograph of the driver imaged by a camera or the like provided around a driver seat of the vehicle. For example, when eyelid movement of the driver is detected and eyes are more closed due to sleepiness, a value of the image analysis information decreases. That is, the image analysis information of the driver has a negative correlation with the sleepiness of the driver.

Next, a description of control performed by the control device 2 when it is determined based on the calculated concentration index CI that the driver feels sleepy will be given. The control device 2 performs control so as to confirm, with the driver, a continuation intention about whether to continue the automatic driving of the vehicle, and to urge improvement of the concentration of the driver when the estimated value y of the concentration index CI is equal to or more than the preset concentration threshold value y1. In this way, by confirming the continuation intention of the automatic driving of the vehicle with the driver, the sleepiness of the driver can be eliminated and the concentration of the driver can be maintained to some extent.

The confirmation of the continuation intention of the automatic driving of the vehicle is a notification given from a voice device provided in the driver seat of the vehicle to the driver by voice or by text displayed on a text display panel. For example, when a decrease in the concentration of the driver is detected, a notification such as "Low driver concentration has been detected. To continue automatic driving, please press the automatic driving continuation switch." is given to the driver to confirm the continuation intention. After the driver presses the automatic driving continuation switch, a notification such as "The intention to continue automatic driving has been confirmed. Automatic driving will continue." is given to the driver.

The control device 2 performs control so as to stop fuel injection toward an engine (internal combustion engine) provided in the vehicle and cancel the automatic driving of the vehicle when the driver does not perform any operation, such as pressing a dedicated switch, and the continuation intention remains in an unconfirmed state for a preset first set time t1 since the continuation intention of the automatic driving of the vehicle was confirmed with the driver.

In this way, by stopping the fuel injection toward the engine and canceling the automatic driving of the vehicle, the vehicle is gradually decelerated, thereby enabling the driver to get rid of the sleepiness and perform an operation to indicate the continuation intention of the automatic driving. As a result, the automatic driving of the vehicle can be resumed in a state where the concentration of the driver is maintained to some extent, and the automatic driving can be continued.

The control device 2 performs control so as to light an emergency flashing indicator light (hazard lamp) of the vehicle and brake and forcibly stop the vehicle when the driver does not perform any operation, such as pressing the dedicated switch, and the continuation intention remains in the unconfirmed state for a preset second set time t2 since the automatic driving of the vehicle was cancelled or when a speed v of the vehicle falls below a preset vehicle speed v1. It should be noted that after the emergency flashing indicator light is lighted, it is preferable to forcibly stop the vehicle automatically from the viewpoint of safety even when there is an operation from the driver.

In this way, when no appropriate response is obtained from the driver even if the vehicle is gradually decelerated, the emergency flashing indicator light of the vehicle is lighted, and the vehicle is braked and forcibly stopped, so that the vehicle is not driven in a state where the driver feels sleepy, and accidents such as a collision between the given vehicle and objects such as another vehicle can be prevented.

As described above, by performing appropriate measures based on the concentration index CI calculated by reflecting the sleepiness of the driver, even when the vehicle is driven automatically, the driving concentration of the driver can be maintained to some extent. As a result, the driving concentration of the driver is maintained to some extent, so that the driver can perform appropriate driving operations, and the vehicle driving authority can be safely and quickly transferred when it is necessary to forcibly transfer the vehicle driving authority from the system to the driver.

Next, a vehicle driving control method according to the present disclosure based on the vehicle driving control system 1 will be described with reference to a control flow of FIG. 7. The control flow of FIG. 7 is a control flow executed from a preceding control flow each time a preset control interval elapses during the automatic traveling of the vehicle.

Figure 7:
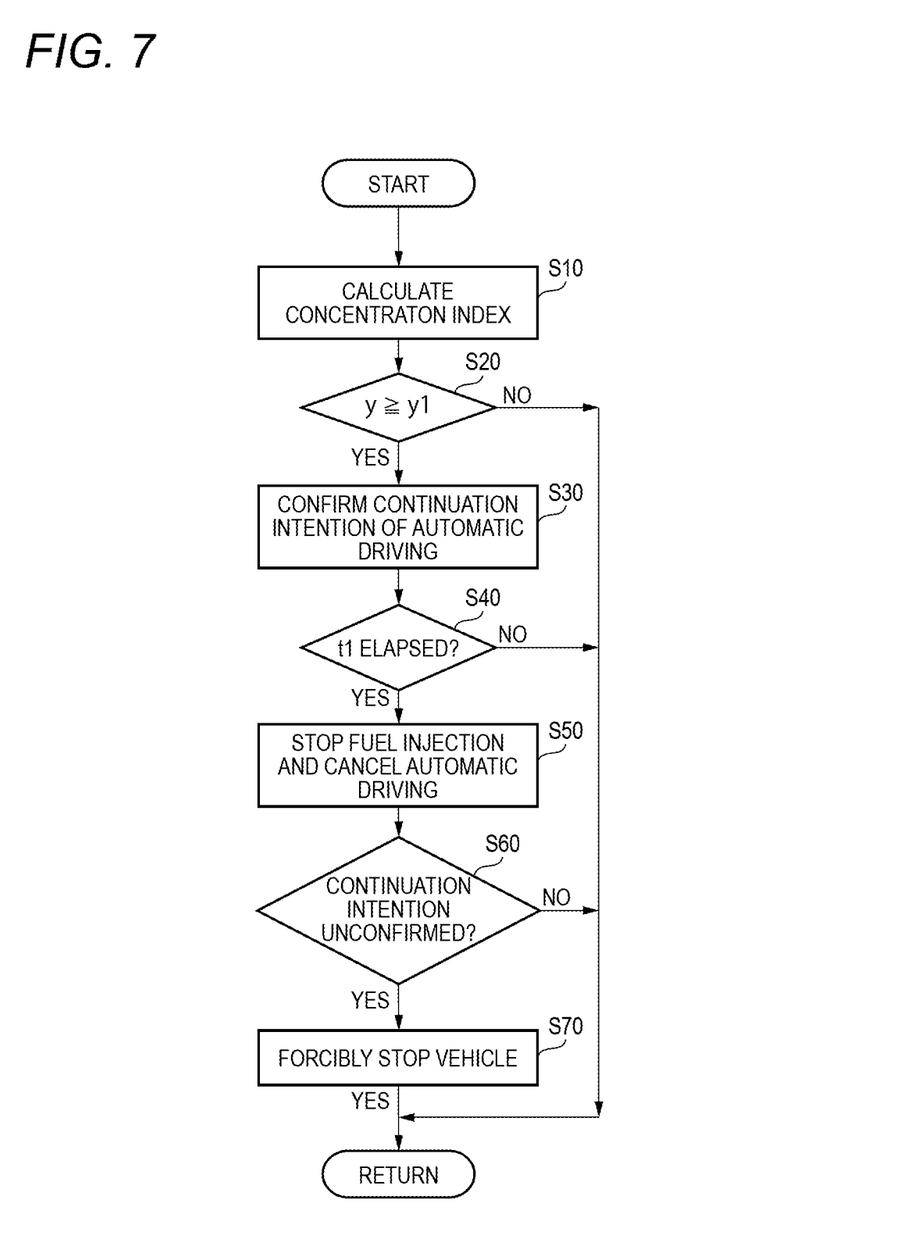
FIG. 7 shows a control flow of a vehicle driving control method according to the present disclosure.

When the control flow of FIG. 7 is started, the estimated value y of the concentration index CI of the driver is calculated in step S10. After the control of step S10 is performed, the process proceeds to step S20. In step S20, it is determined whether the estimated value y calculated in step S10 is equal to or more than the concentration threshold value y1. If the estimated value y is less than the concentration threshold value y1 (NO), the process returns, and the control flow is ended. Meanwhile, if the estimated value y is equal to or more than the concentration threshold value y1 (YES), the process proceeds to step S30, and in step S30, the continuation intention about whether to continue the automatic running of the vehicle is confirmed with the driver to improve the concentration of the driver. After the control of step S30 is performed, the process proceeds to step S40.

In step S40, it is determined whether the preset first set time t1 elapses since the continuation intention of the automatic driving of the vehicle was confirmed with the driver, the driver does not perform any operation, such as pressing the dedicated switch, and the continuation intention remains in the unconfirmed state. If the first set time t1 has not elapsed (NO), the process returns, and the control flow is ended. Meanwhile, if the first set time t1 has elapsed (YES), the process proceeds to step S50, and in step S50, the fuel injection toward the engine is stopped, and the automatic driving of the vehicle is cancelled. After the control of step S50 is performed, the process proceeds to step S60.

In step S60, it is determined whether the driver does not perform any operation, such as pressing the dedicated switch, and the continuation intention remains in the unconfirmed state since the automatic driving of the vehicle was cancelled. This determination is made based on whether the preset second set time t2 elapses since the automatic driving of the vehicle was cancelled while the continuation intention remains in the unconfirmed state or whether the speed v of the vehicle falls below the preset vehicle speed v1. If the continuation intention of the automatic driving is confirmed (NO), the process returns, and the control flow is ended. Meanwhile, if the continuation intention of the automatic driving is not confirmed (YES), the process proceeds to step S70, and in step S70, the emergency flashing indicator light (hazard lamp) of the vehicle is lighted and the vehicle is braked and forcibly stopped. After the control of step S70 is performed, the process returns, and the control flow is ended.

As described above, the vehicle driving control method based on the vehicle driving control system 1 according to the present disclosure is a vehicle driving control method which has a function of automatically driving a vehicle, in which the control is performed so as to detect the brain wave or the heartbeat of the driver of the vehicle during the automatic driving of the vehicle, and use the plurality of indexes further correlated with the sleepiness of the driver among the indexes related to the brain wave or the heartbeat of the driver to calculate the concentration index CI, which is the index indicating the driving concentration of the driver, at each preset control interval.

According to this method, the same effect as those of the vehicle driving control system 1 can be obtained.

In the above description, attention is paid to the control device 2 provided in the driving control system 1, and the function realized by the control device 2 and the processing executed by the control device 2 are described.

Specifically, the control device 2 may be implemented, for example, by the following configuration. That is, the control device 2 is connected to various devices provided in the vehicle by wireless or wired connection, and can be configured to include an interface which transmits and receives a signal configured to communicate with the various devices, a memory which stores information, and a controller.

The various devices include, for example: an operation unit such as a button, a switch, and a touch panel operated by the driver or an occupant of the vehicle 3; a display which displays a screen; a speaker which outputs voice; a microphone which receives voice commands from the driver or the occupant; a biological index sensor which detects the brain wave or a heart rate of the driver; an in-vehicle camera which images and monitors a driving state of the driver, and the like.

The various devices include, for example: various actuators configured to control the driving state of the vehicle; a brake system of the vehicle; an engine control system of the vehicle; a lighting device provided in the vehicle, such as a light, a rear lamp, a hazard lamp or the emergency flashing indicator light; a vehicle speed sensor which measures the vehicle speed of the vehicle; an acceleration sensor or an impact sensor which measures acceleration or impact occurring in the vehicle; a steering angle sensor which measures a steering angle of the vehicle; a driving camera or radar which detects a driving environment of the vehicle, and the like.

The interface includes a communication module configured to communicate with the various devices, and may be connected to the various devices by wired connection, for example, by including a connector, or may be wirelessly connected to the various devices, for example, by including a wireless communication module.

The memory may include a semiconductor storage device such as a rewritable DRAM or EPROM, or a non-rewritable ROM, or may include a storage device such as a hard disk.

The controller is connected to the interface and the memory. The controller may be configured, for example, by a processor, and may be configured to execute a series of processing by executing a program stored in the memory, or may be configured as hardware such as an ASIC and configured to execute a predetermined series of processing.

The controller repeats the following processing for each preset control interval while the vehicle is driven automatically: acquiring, via the interface, a biological index signal output from the biological index sensor among the devices, which detects the brain wave or the heart rate of the driver of the vehicle, detecting the brain wave or the heart rate of the driver based on the acquired biological index signal, calculating a plurality of biological indexes correlated with sleepiness of the driver based on the detected brain wave or heart rate of the driver, and using at least two of the plurality of calculated biological indexes to calculate the concentration index, which is the index indicating the driving concentration of the driver.

This application is based on JP-A-2017-094575 filed on May 11, 2017, the contents of which are incorporated herein by reference.

INDUSTRIAL APPLICABILITY

According to the present disclosure, appropriate measures can be performed to maintain driving concentration of a driver to some extent based on a calculated concentration index. The driving concentration of the driver can be maintained to some extent even during automatic driving of the vehicle. Since the driving concentration of the driver is maintained to some extent, the driver can perform appropriate driving operations, and vehicle driving authority can be safely and quickly transferred when it is necessary to forcibly transfer the vehicle driving authority from a system to the driver.

REFERENCE SIGNS LIST

1 Vehicle driving control system
2 Control device
CI Concentration index
y Estimated value of concentration index
y1 Concentration threshold value
v Vehicle speed
v1 Set vehicle speed

The invention claimed is:
1. A vehicle driving control system which is configured to have a function of automatically driving a vehicle, wherein
a processor which controls the driving control system is configured to perform control so as to detect a brain wave or a heartbeat of a driver of the vehicle during automatic driving of the vehicle, calculate a concentration index, which is an index indicating driving concentration of the driver by using a plurality of indexes correlated with sleepiness of the driver among indexes related to the brain wave or the heartbeat of the driver, at each preset control interval, urge improvement of the concentration of the driver by confirming with the driver a continuation intention about whether to continue the automatic driving of the vehicle, when the concentration index is equal to or more than a preset concentration threshold value, and continue the automatic driving of the vehicle based on the continuation intention for continuing the automatic driving.

2. The vehicle driving control system according to claim 1, wherein the processor is configured to perform control so as to cancel the automatic driving of the vehicle by stopping fuel injection toward an internal combustion engine provided in the vehicle, when the continuation intention remains in an unconfirmed state for a preset first set time since the continuation intention was provided to the driver.

3. The vehicle driving control system according to claim 2, wherein the processor is configured to perform control so as to brake and stop the vehicle while lighting an emergency flashing indicator light of the vehicle, when the continuation intention remains in the unconfirmed state for a preset second set time since the automatic driving of the vehicle was cancelled or when a speed of the vehicle falls below a preset vehicle speed.

4. A vehicle driving control method which has a function of automatically driving a vehicle, comprising:

detecting a brain wave or a heartbeat of a driver of the vehicle during automatic driving of the vehicle;

calculating a concentration index which is an index indicating driving concentration of the driver by using a plurality of indexes correlated with sleepiness of the driver among indexes related to the brain wave or the heartbeat of the driver, at each preset control interval;

urging improvement of the concentration of the driver by confirming with the driver a continuation intention about whether to continue the automatic driving of the vehicle, when the concentration index is equal to or more than a preset concentration threshold value; and continuing the automatic driving of the vehicle based on the continuation intention for continuing the automatic driving.

5. A vehicle driving control system which automatically drives a vehicle, comprising:

an interface which is connected to a device provided in the vehicle by wireless or wired connection, and the interface transmits and receives a signal configured to communicate with the device;

a memory which stores information; and a processor which repeats following processing for each preset control interval while the vehicle is driven automatically:

acquiring, via the interface, a biological index signal output from a biological index sensor of the device, which detects a brain wave or a heart rate of a driver of the vehicle;

detecting the brain wave or the heart rate of the driver based on the acquired biological index signal;

calculating a plurality of biological indexes correlated with sleepiness of the driver based on the detected brain wave or detected heart rate of the driver;

calculating a concentration index which is an index indicating driving concentration of the driver by using at least two of the plurality of calculated biological indexes;

urging improvement of the concentration of the driver by confirming with the driver a continuation intention about whether to continue the automatic driving of the vehicle, when the concentration index is equal to or more than a preset concentration threshold value; and continuing the automatic driving of the vehicle based on the continuation intention for continuing the automatic driving.

6. The vehicle driving control system according to claim 5, wherein the plurality of biological indexes include at least two of:

a standard deviation of $\alpha$ waves of the brain wave of the driver;

an average of $\beta$ waves of the brain wave of the driver;

a heartbeat peak value interval of the driver; and a standard deviation of the heartbeat peak value interval of the driver.

7. The vehicle driving control system according to claim 5, wherein the processor further performs following processing:

determining whether the calculated concentration index is equal to or more than the preset concentration threshold value; and confirming, by controlling the device via the interface, with the driver the continuation intention about whether to continue the automatic driving of the vehicle when it is determined that the calculated concentration index is equal to or more than the preset concentration threshold value.

8. The vehicle driving control system according to claim 7, wherein the processor further performs following processing:

determining whether a signal indicating the continuation intention is received from the device via the interface; and performing control so as to cancel the automatic driving of the vehicle by controlling the device via the interface, when a signal indicating a confirmation result is not received after elapse of a preset first set time since the continuation intention about whether to continue the automatic driving of the vehicle was provided to the driver.

9. The vehicle driving control system according to claim 8, wherein the processor further performs following processing:

performing control so as to brake and stop the vehicle while lighting an emergency flashing indicator light of the vehicle by controlling the device via the interface, after elapse of a preset second set time since the control of cancelling the automatic driving of the vehicle was performed or when a driving speed of the vehicle is equal to or less than a preset driving speed based on a signal indicating the driving speed of the vehicle received via the interface.

* * * * *